United States Patent [19]

Muller et al.

[11] Patent Number: 5,486,155
[45] Date of Patent: Jan. 23, 1996

[54] ROTATABLE ENDOSCOPE SHEATH

[75] Inventors: Richard P. Muller, Bronx, N.Y.; Richard J. O'Hare, Wilton, Conn.

[73] Assignee: Circon Corporation, Santa Barbara, Calif.

[21] Appl. No.: 275,845

[22] Filed: Jul. 15, 1994

[51] Int. Cl.$^6$ .................. A61B 1/012; A61B 1/307
[52] U.S. Cl. .................. 600/137; 600/105; 600/135; 600/138
[58] Field of Search .................. 606/27, 28, 29, 606/39, 46, 170; 128/4, 6, 7; 604/158; 600/105, 135, 137, 138, 153, 156

[56] References Cited

U.S. PATENT DOCUMENTS

| | | | |
|---|---|---|---|
| 2,031,682 | 2/1936 | Wappler et al. | 174/89 |
| 2,442,966 | 6/1948 | Wallace | 128/303.15 |
| 2,448,741 | 9/1948 | Scott et al. | 128/303.15 |
| 2,487,502 | 11/1949 | Willinsky | 128/303.15 |
| 2,990,830 | 7/1961 | Hett | 128/4 |
| 3,144,020 | 8/1964 | Zingale | 128/4 |
| 3,149,633 | 9/1964 | Zingale | 128/303.15 |
| 3,752,159 | 8/1973 | Wappler | 128/303.15 |
| 3,850,162 | 11/1974 | Iglesias | 128/6 |
| 3,939,840 | 2/1976 | Storz | 128/303.15 |
| 3,990,456 | 11/1976 | Iglesias | 128/303.15 |
| 4,132,227 | 1/1979 | Ibe | 128/4 |
| 4,149,538 | 4/1979 | Mrava et al. | 128/303.15 |
| 4,538,610 | 9/1985 | Kubota | 128/303.15 |
| 4,567,880 | 2/1986 | Goodman | 128/7 |
| 4,625,713 | 12/1986 | Hiraoka | 128/4 |
| 4,633,882 | 1/1987 | Matsuo et al. | 128/660 |
| 4,657,018 | 4/1987 | Hakky | 128/303.15 |
| 4,726,370 | 2/1988 | Karasawa et al. | 128/303.15 |
| 4,765,314 | 8/1988 | Kolditz et al. | 128/4 |
| 4,819,620 | 4/1989 | Okutsu | 128/4 |
| 4,904,246 | 2/1990 | Atkinson | 604/264 |
| 4,919,131 | 4/1990 | Grossi et al. | 606/46 |
| 4,920,961 | 5/1990 | Grossi et al. | 606/14 |
| 4,955,884 | 9/1990 | Grossi et al. | 606/46 |
| 5,184,602 | 2/1993 | Anapliotis et al. | 128/6 |
| 5,287,845 | 2/1994 | Faul et al. | 128/7 |

*Primary Examiner*—Richard J. Apley
*Assistant Examiner*—Beverly M. Flanagan
*Attorney, Agent, or Firm*—Perman & Green

[57] ABSTRACT

A continuous flow resectoscope having a working element and a sheath assembly removably connected to the working element. The sheath assembly has an outer sheath removably attached to an inner sheath. The improvement comprises a rotatable connection of the inner sheath to the working element, wherein the working element is rotatable relative to both the inner and outer sheaths.

16 Claims, 2 Drawing Sheets

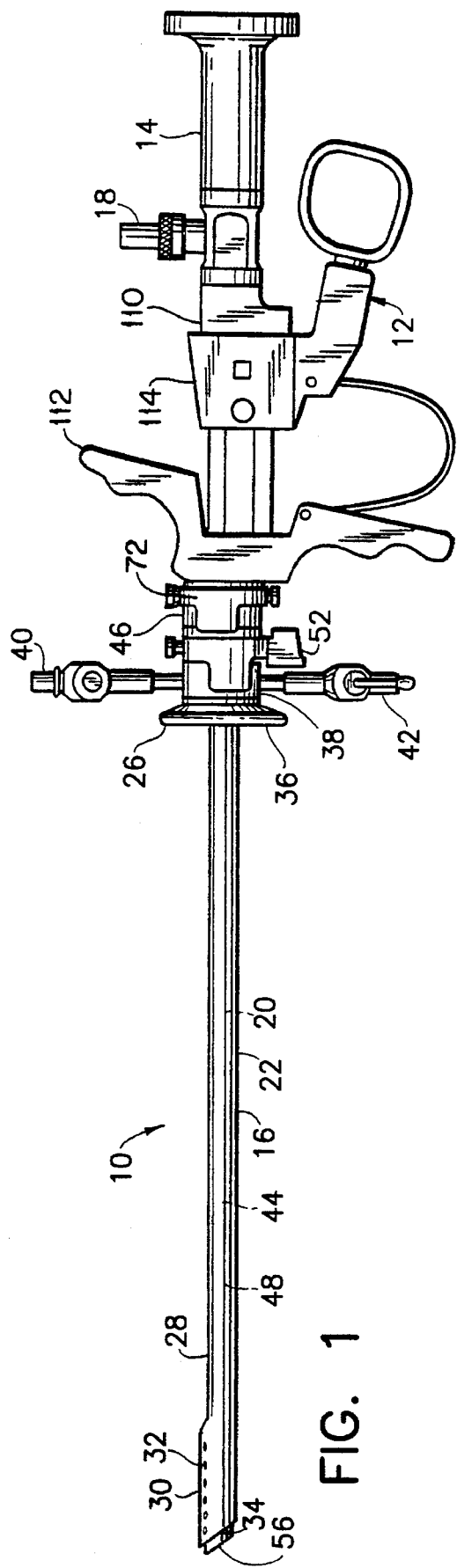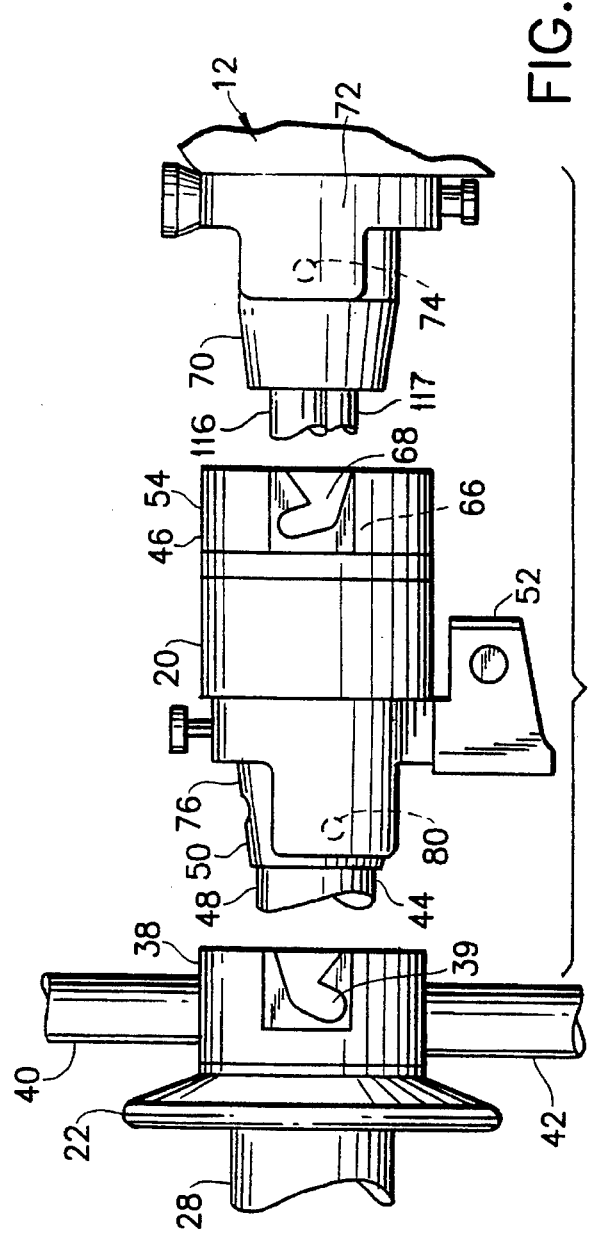

ROTATABLE ENDOSCOPE SHEATH

BACKGROUND OF THE INVENTION

1. Field of the Invention

The present invention relates to medical endoscopes and, more particularly, to an endoscope with a rotatable sheath.

2. Prior Art

U.S. Pat. No. 4,920,961 discloses a latching system for connecting inner and outer sheaths to each other and for connecting the inner sheath to a working element. U.S. Pat. No. 4,132,227 discloses a continuous flow urological endoscope sheath. U.S. Pat. No. 5,287,845 discloses a continuous flow urological endoscope with a rotatable outer sheath. A problem exists with the sheath assembly disclosed in U.S. Pat. No. 5,287,845 in that the inner sheath is rotated with the working element when the working element is rotated. Because the front end of the inner sheath is located past the end of the outer sheath and has a non-uniform or angled shape, the end of the inner sheath can cause damage to tissue when it is rotated inside a patient's body.

SUMMARY OF THE INVENTION

In accordance with one embodiment of the present invention an endoscope is provided comprising a working element and a first sheath. The first sheath covers a portion of the working element and has a first section and a second section. The first section has a tube. The second section is rotatably attached directly to the first section and includes means for directly connecting the working element to the second section. The working element is rotatable relative to the tube.

In accordance with another embodiment of the present invention, in a continuous flow resectoscope having a working element and a sheath assembly removably connected to the working element, the sheath assembly having an outer sheath removably attached to an inner sheath, the improvement comprises a rotatable connection of the inner sheath to the working element, wherein the working element is rotatable relative to both the inner and outer sheaths.

In accordance with another embodiment of the present invention, in a system for connecting an endoscope sheath to a working element, the sheath having an end with a connector section having latch slots, the working element having a movable latch adapted to make a stationary but removable connection with the sheath's connector, the improvement comprising an adapter located between and connecting the connector of the sheath with the latch of the working element. The adaptor includes a rotatable section such that the working element is rotatable relative to the sheath.

BRIEF DESCRIPTION OF THE DRAWINGS

The foregoing aspects and other features of the present invention are explained in the following description, taken in connection with the accompanying drawings, wherein:

FIG. 1 is an elevational side view of a resectoscope incorporating features of the present invention;

FIG. 2 is an exploded elevational side view of a connection area of the resectoscope shown in FIG. 1;

DETAILED DESCRIPTION OF THE PREFERRED EMBODIMENTS

Figure 3A:
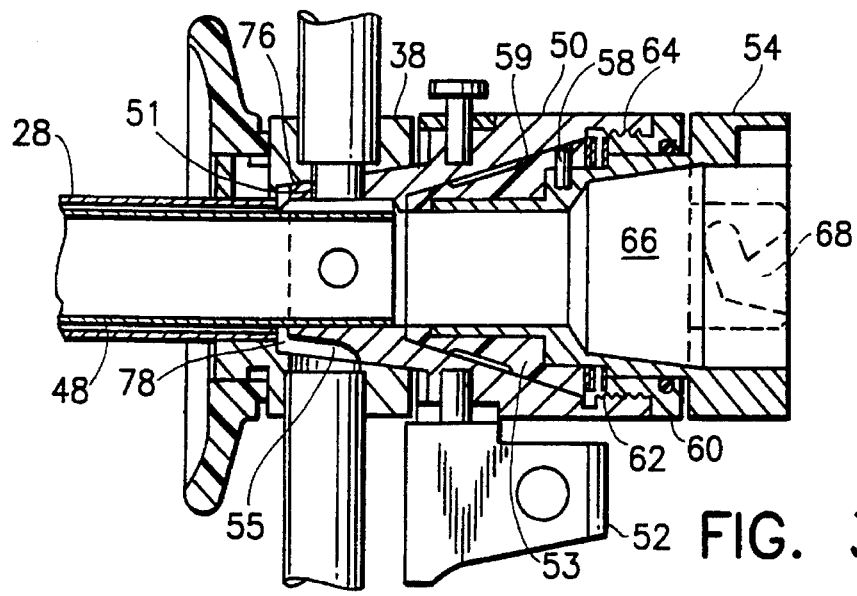
FIG. 3A is a cross-sectional side view of the rear end of the sheath assembly of the resectoscope shown in FIG. 1.

Referring to FIG. 1, there is shown an elevational side view of a resectoscope 10 incorporating features of the present invention. Although the present invention will be described with reference to the embodiments shown in the drawings, features of the present invention can be embodied in various different forms of alternate embodiments and alternate types of endoscopes. In addition, any suitable size, shape or type of elements or materials could be used.

The resectoscope 10 generally comprises a working element 12, a telescope 14, a sheath assembly 16, and a through-put device (not shown). The through-put device is a tool, such as an electrode or a fiber optic laser guide. The working element 12 and telescope 14, in the embodiment shown, are a USA ELITE SYSTEM working element and telescope. USA ELITE SYSTEM is a trademark of Circon Corporation of Santa Barbara, Calif. The telescope 14 is removably mounted to the working element 12 and has a connector 18 for connecting fiber optics of the telescope 14 with a light source (not shown). The working element 12 generally comprises a frame 110, a front handle 112, a movable portion 114, cone connector 70 (see FIG. 2), latch assembly 72, and guide tubes 116, 117 (see FIG. 2). The working element 12, telescope 14 and through-put devices are well known in the art. In alternate embodiments, any suitable type of working element, telescope and/or through-put device could be used.

The sheath assembly 16, in the embodiment shown, is a continuous flow sheath assembly which comprises an inner sheath 20 and an outer sheath 22. The outer sheath 22 has a tube 28 and a rear end section 26. The outer sheath 22 has a front that is formed by the front end 30 of the tube 28. The front end 30 has holes 32 and a front aperture 34. The rear end section 26 is attached to the rear end of the tube 28. The rear end section 26 has a shield 36, a connector 38, a fluid inlet 40 and a fluid outlet 42. The outer sheath 22 is substantially identical to the outer sheath described in U.S. Pat. No. 4,920,961 which is hereby incorporated by reference in its entirety. In alternate embodiments, other types of outer sheaths could be provided.

Referring also to FIG. 2, the inner sheath is similar, but different to the inner sheath described in U.S. Pat. No. 4,920,961. The inner sheath 20 has a first section 44 and a second section 46. The first section 44 generally comprises a tube 48, a first frame member 50, and a movable latch 52. The second section 46 generally comprises a bearing 53 (see FIG. 3A) and a second frame member 54. The tube 48 is located inside the tube 28, but has a front end 56 that projects out of the front aperture 34 of the outer sheath tube 28. The rear end of the tube 48 is fixedly connected to the first frame member 50. The latch 52 is movably mounted on the first frame member 50. The latch 52 is substantially identical to the latch assembly of the inner sheath disclosed in U.S. Pat. No. 4,920,961. The latch 52 is adapted to make a stationary, but removable connection of the first frame member 50 relative with the connector 38 by snap-lock engaging side notches 39. In alternate embodiments, other types of latching or connecting mechanisms could be used.

Referring now also to FIG. 3A, a cross-sectional view of the rear ends of the assembled outer and inner sheaths 20, 22 is shown. The second frame member 54 is rotatably connected to the first frame member 50 by the bearing 53. The bearing 53, in the embodiment shown, is a sleeve bearing made of a suitable material, such as tetrafluoroethylene or other suitable bearing material. The bearing 53 is fixedly attached to a front end of the second frame member 54 by a pin 58. The bearing 53 has a general cone shaped exterior that matingly engages a cone shaped receiving area 59 in the first frame member 50. A connecting sleeve 60 and a wave spring 62 are provided to connect the bearing 53 to the first frame member 50 and, thus, connect the second frame member 54 to the first frame member 50. The connecting sleeve 60 is screwed into the rear end of the first frame member 50 at threaded area 64. The wave spring 62 is located between the front of the connecting sleeve 60 and the rear end of the sleeve bearing 53. When the connecting sleeve 60 is fully connected to the first frame member 50, the wave spring 62 is compressed between the connecting sleeve 60 and the sleeve bearing 53. This biases the sleeve bearing 53 against the cone shaped walls of the receiving area 59. This forms a seal between the sleeve bearing 53 and the first frame member 50. The connecting sleeve 60 is rotatable relative to the second frame member 54.

The second frame member 54 has an interior receiving area 66 and two exterior side notches 68. The interior receiving area 66 is suitably sized and shaped to matingly receive the cone connector 70 of the working element 12 therein. The side notches 68 are suitably configured to be used with inwardly facing pins 74 of the latch assembly 72 of the working element 12 to stationarily, but removably snap-lock connect the second frame member 54 with the frame of the working element 12.

As noted above, the first frame member 50 of the inner sheath 20 is stationarily connected to the connector 38 of the outer sheath 22. This connection is made by means of the cone section 76 of the first frame member 50 being matingly received in the receiving area 78 of the connector 38 and, latching of inwardly facing pins 80 of the latch 52 with the exterior side notches 39 of the connector 38. Also as noted above, the second frame member 54 of the inner sheath 20 is stationarily connected to the frame of the working element 12. This connection is made by means of the cone connector 70 being matingly received in the receiving area 66 and, latching of the inwardly facing pins 74 of the latch assembly 72 with the exterior side notches 68 of the second frame member 54. Because of the rotatable connection of the first frame member 50 to the second frame member 54, the working element 12 is able to rotate relative to the first frame member 50. Therefore, the working element 12 is able to rotate relative to the outer sheath 22 and the tube 48 of the inner sheath 20. The second frame member 54 and sleeve bearing 53 rotate with the working element 12. The sleeve bearing 53, biased by the wave spring 62 against the first frame member 50, maintains a seal between the first and second frame members.

As noted above, U.S. Pat. No. 5,287,845 discloses a continuous flow urological endoscope with a rotatable outer sheath. However, the inner sheath is not rotatable relative to the working element. The problem of potential tissue damage to a patient is noted in the Prior Art section above. The present invention, on the other hand, provides a rotatable connection between the working element 12 and both the outer sheath 22 and the tube 48 of the inner sheath 20. Hence, both the front 30 of the outer sheath 22 and the front 56 of the inner sheath 20 can remain in a constant position and orientation relative to each other and the patient as the working element is rotated by a user. This helps to prevent inadvertent tissue damage to the patient.

Figure 3B:
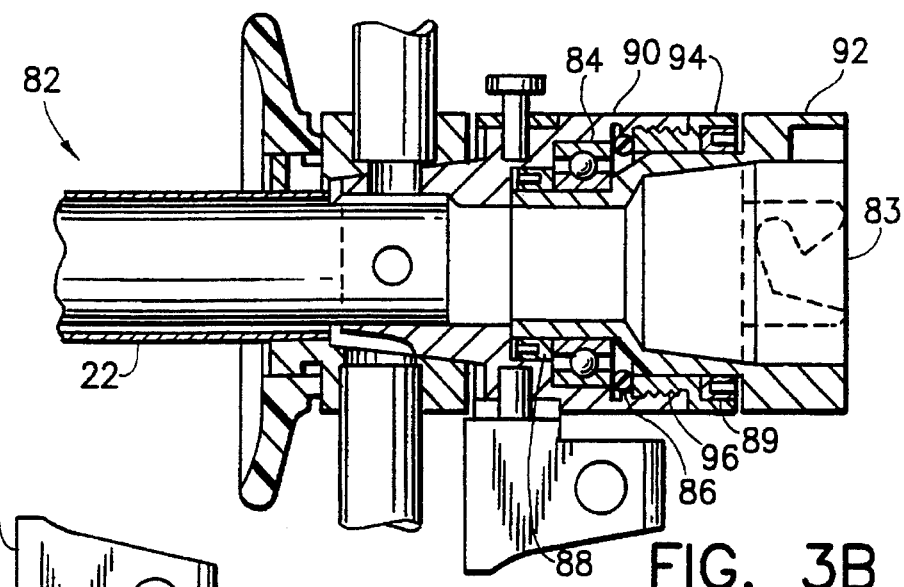
FIG. 3B is a cross-sectional side view as in FIG. 3A of an alternate embodiment of the present invention.

Referring now to FIG. 3B, a cross-sectional view of an alternate embodiment of a sheath assembly 82 is shown with the outer sheath 22 and an inner sheath 83. The sheath assembly 82 is similar to the sheath assembly 16. However, rather than a sleeve bearing and wave spring, the sheath assembly 82 has a roller bearing 84, O-ring seal 86, and seals 88, 89. The roller bearing 84 and seals 86, 88, 89 are sandwiched between the first frame member 90 and second frame member 92. A sleeve connector 94 that is fixedly connected to the first frame member 90 at threaded area 96 keeps the two frame members connected to each other. This embodiment is intended to illustrate that different configurations could be used to rotatably connect the sheath assembly to the working element.

Figure 4:
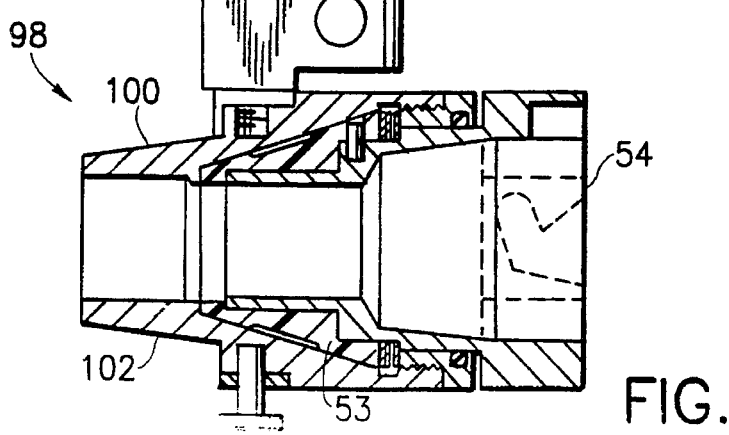
FIG. 4 is a cross-sectional side view of another alternate embodiment of the present invention.

Referring now to FIG. 4, another alternate embodiment of the present invention is shown. The embodiment shown is an adaptor 98 for rotatably connecting a prior art non-rotatable or partially rotatable sheath or sheath assembly to a working element. The adaptor 98 includes a first frame member 100, a second frame member 54, a sleeve bearing 53, and a latch assembly 52. The adaptor 98 is substantially the same as the rear end of the inner sheath 20 shown in FIG. 3A. However, the first frame member 100 does not have an inner tube attached to it, does not have a fluid inlet channel 51 or a fluid outlet channel 55 (see FIG. 3A) through its cone section 102, and its cone section 102 is suitably sized and shaped to be received in a receiving area of the prior art sheath. The adaptor 98 could be used with old working elements and sheaths or sheath assemblies, such as those disclosed in U.S. Pat. No. 4,920,961, to provide rotational movement of the working element relative to the sheath(s). The adaptor 98 could also be sold as part of a new resectoscope to allow a user to readily convert a resectoscope between rotational and non-rotational configurations.

It should be understood that the foregoing description is only illustrative of the invention. Various alternatives and modifications can be devised by those skilled in the art without departing from the spirit of the invention. Accordingly, the present invention is intended to embrace all such alternatives, modifications and variances which fall within the scope of the appended claims.

What is claimed is:

1. An endoscope comprising:

a working element; and a first sheath covering a portion of the working element, the first sheath having a first section and a second section, the first section having a tube and means for connecting a second sheath over a portion of the tube, the second section being rotatably attached directly to the first section and being directly stationarily connected to the working element, wherein the working element is rotatable relative to the tube.

2. An endoscope as in claim 1 further comprising a second sheath surrounding the tube of the first sheath.

3. An endoscope as in claim 2 wherein the first and second sheaths are connected to each other to form a continuous flow sheath assembly.

4. An endoscope as in claim 1 wherein the first section includes a first frame member fixedly connected to an end of the tube and the second section includes a second frame member rotatably connected to the first frame member by a rotator.

5. An endoscope as in claim 4 wherein the rotator comprises a sleeve bearing fixedly connected to the second frame member and sandwiched between the first and second frame members.

6. An endoscope as in claim 4 wherein the rotator comprises a roller bearing between the first and second frame members.

7. An endoscope as in claim 4 wherein the second frame member includes latch slots having a latch of the working element connected thereto.

8. An endoscope as in claim 4 wherein the means for connecting a second sheath over a portion of the tube includes a movable latch connected to the first frame member.

9. In a continuous flow resectoscope having a working element and a sheath assembly removably connected to the working element, the sheath assembly having an outer sheath with an outer tube removably connected to an inner sheath, the improvement comprising:

a rotatable connection of an inner tube of the inner sheath to the working element, wherein the working element is rotatable relative to both the inner and outer tubes of both sheaths.

10. A resectoscope as in claim 9 wherein the rotatable connection comprises the inner sheath having a first frame member fixedly connected to an end of the inner tube, and a second frame member rotatably attached to the first frame member.

11. A resectoscope as in claim 10 wherein the inner sheath has a sleeve bearing sandwiched between the first and second frame members.

12. A resectoscope as in claim 10 wherein the inner sheath has at least one roller bearing between the first and second frame members.

13. A resectoscope as in claim 10 wherein the inner sheath includes a movable latch on the first frame member connecting the first frame member to the outer sheath.

14. A resectoscope as in claim 10 wherein the inner sheath includes latch slots on the second frame member connecting the second frame member to the working element.

15. In a system for connecting an endoscope sheath to a working element, the improvement comprising:

an adaptor located between a connector section of the sheath and the working element, the adaptor being separately removably connected to the connector section of the sheath and the working element and, including a rotatable section such that the working element is rotatable relative to the sheath.

16. In a continuous flow resectoscope having a working element and a sheath assembly removably connected to the working element, the sheath assembly having an outer sheath with an outer tube removably connected to an inner sheath with an inner tube, the improvement comprising:

a rotatable connection of the inner tube to the working element, wherein the working element is rotatable relative to both the inner and outer tubes and the rotatable connection comprises the inner sheath having a first frame member fixedly connected to an end of the inner tube, and a second frame member rotatably attached to the first frame member.

* * * * *